(12) United States Patent
Cheah et al.

(10) Patent No.: US 6,828,433 B2
(45) Date of Patent: Dec. 7, 2004

(54) DNA ENCODING MUTATED COLLAGEN X

(75) Inventors: Kathryn S. E. Cheah, Hong Kong (HK); Kenneth M. C. Cheung, Hong Kong (HK)

(73) Assignee: The University of Hong Kong, Hong Kong (CN)

(*) Notice: Subject to any disclaimer, the term of this patent is extended or adjusted under 35 U.S.C. 154(b) by 94 days.

(21) Appl. No.: 09/975,607

(22) Filed: Oct. 11, 2001

(65) Prior Publication Data
US 2002/0115608 A1 Aug. 22, 2002

Related U.S. Application Data

(63) Continuation of application No. 09/415,551, filed on Oct. 8, 1999, now Pat. No. 6,369,295.
(60) Provisional application No. 60/103,550, filed on Oct. 8, 1998.

(51) Int. Cl.$^7$ ............... C07H 21/02; C12N 15/63; C12N 15/85; C12N 1/20
(52) U.S. Cl. ............... 536/23.1; 435/320.1; 435/455; 435/325; 435/252.1
(58) Field of Search ............ 536/23.5; 435/320.1, 435/70.1, 71.1

(56) References Cited
PUBLICATIONS

Jacenko et al. Nature, 1993, 365: 56–61.*
Warman et al. Nature Genetics, 1993, 5: 79–82.*

\* cited by examiner

*Primary Examiner*—Michael C. Wilson
(74) *Attorney, Agent, or Firm*—Robert D. Katz; Cooper & Dunham LLP

(57) ABSTRACT

This invention provides an isolated DNA comprising the sequence which codes for a mutated collagen X or a portion thereof wherein the expression of said DNA regulates bone growth. This invention provides a polypeptide encoded by the isolated DNA comprising the sequence which codes for a mutated collagen X or a portion thereof wherein the expression of said DNA regulates bone growth. This invention also provides a polypeptide which comprise the portion of the mutated collagen X capable of regulating bone growth. This invention further provides a transgenic animal comprising an isolated DNA comprising the sequence which codes for a mutated collagen X or a portion thereof wherein the expression of said DNA regulates bone growth.

4 Claims, 9 Drawing Sheets

Figure 2

```
    GTC ATG CCT GAT GGC TTC ATA AAG GCA GGC CAG AGG CCC AGG CTT TCT GGG ATG CCG CTT
    val met pro asp gly phe ile lys ala gly gln arg pro arg leu ser gly met pro leu     mouse wt 540
    GTC AGT GCT AAC CAC GGG GTA ACA GGT ATG CCC GTG TCT GCT TTT ACT GTC ATT CTC TCT
    val ser ala asn his gly val thr gly met pro val ser ala phe thr val ile leu ser     mouse wt 560
    AAA GCT TAC CCA GCA GTA GGT GCC CCC ATC CCA TTT GAT GAG ATT CTG TAC AAT AGG CAG
    lys ala tyr pro ala val gly ala pro ile pro phe asp glu ile leu tyr asn arg gln     mouse wt 580
    CAG CAT TAC GAC CCA AGA TCT GGT ATC TTT ACC TGT AAG ATC CCA GGC ATA TAC TAT TTC
    gln his tyr asp pro arg ser gly ile phe thr cys lys ile pro gly ile tyr tyr phe     mouse wt 600
    TCC TAC CAC GTG CAT GTG AAA GGG ACT CAC GTT TGG GTA GGC CTG TAT AAG AAC GGC ACG
    ser tyr his val his val lys gly thr his val trp val gly leu tyr lys asn gly thr     mouse wt ACA
                                                                              thr          mouse 13del
                                                                              thr          human 13del 620
    CCT ACG ATG TAC ACG TAT GAT GAG TAC AGC AAA GGC TAC CTG GAT CAG GCT TCA GGG AGT
    pro thr met tyr thr tyr asp glu tyr ser lys gly tyr leu asp gln ala ser gly ser       mouse wt CGT ATG ATG AGT ACA GCA AAG GCT ACC TGG ATC AGG CTT CAG GGA GTG CAA TCA TGG AGC
    arg met met ser thr ala lys ala thr trp ile arg leu gln gly val gln ser trp ser       mouse 13del
    pro met met asn thr pro lys ala thr trp ile arg leu gln gly val pro ser ser ile       human 13del 640
    GCA ATC ATG GAG CTC ACA GAA AAT GAC CAG GTA TGG CTC CAA TTG CCC AAT GCA GAA TCA
    ala ile met glu leu thr glu asn asp gln val trp leu gln leu pro asn ala glu ser       mouse wt TCA CAG AAA ATG ACC AGG TAT GGC TCC AAT TGC CCA ATG CAG AAT CAA ACG GCC TCT ACT
    ser gln lys met thr arg tyr gly ser asn cys pro met gln asn gln thr ala ser thr       mouse 13del
    ser gln lys met thr arg cys gly ser ser phe pro met pro ser gln met ala tyr thr       human 13del 660
    AAC GGC CTC TAC TCC TCT GAG TAC GTC CAC TCG TCC TTC TCA GGA TTC CTA GTG GCT CCC
    asn gly leu tyr ser ser glu tyr val his ser ser phe ser gly phe leu val ala pro       mouse wt 671
    CCT CTG AGT ACG TCC ACT CGT CCT TCT CAG GAT TCC TAG
    pro leu ser thr ser thr arg pro ser gln asp ser STOP                                  mouse 13del
    pro leu ser met ser thr pro leu ser gln asp ser STOP                                  human 13del 680
    ATG TGA
    met STOP                                                                              mouse wt
```

Figure 4
Fig. 4b
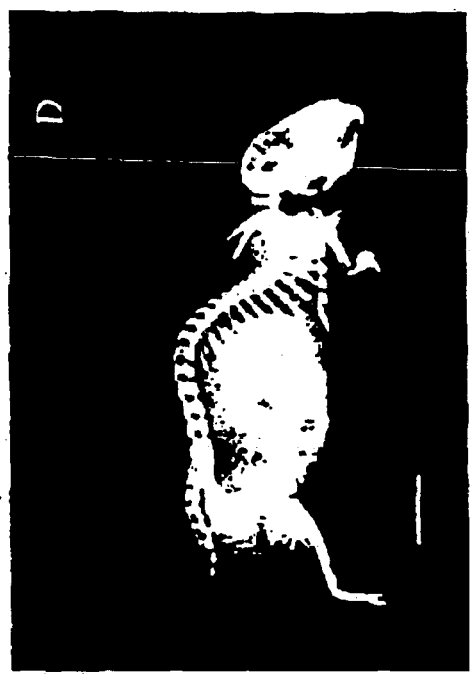
Fig. 4d
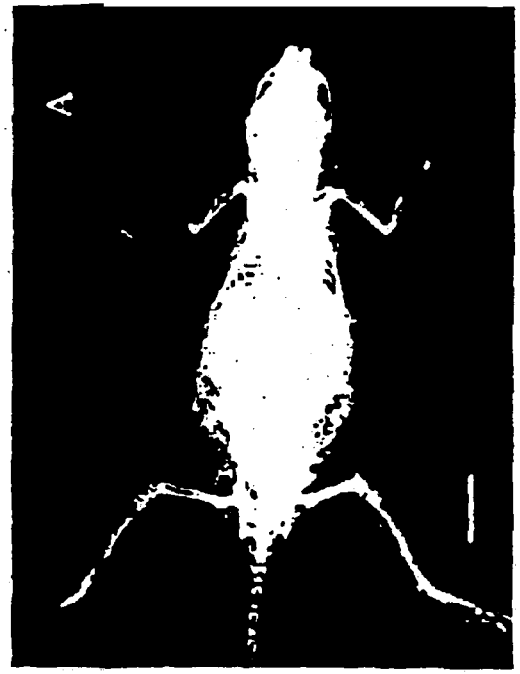
Fig. 4a
Fig. 4c

Figure 5
Fig. 5b
Fig. 5d
Fig. 5a
Fig. 5c

Figure 6
Fig. 6b
Fig. 6d
Fig. 6a
Fig. 6c

Figure 9
Fig 9a
(100X)
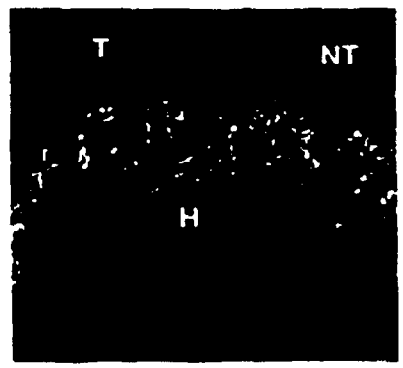
Fig 9b
(100X)
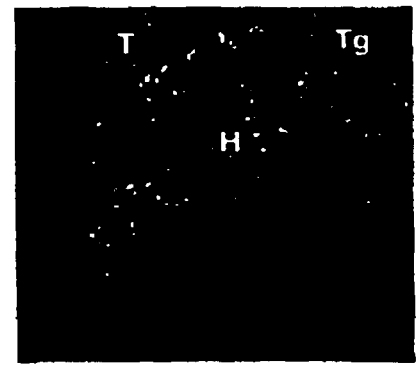
Fig 9c
(100x)
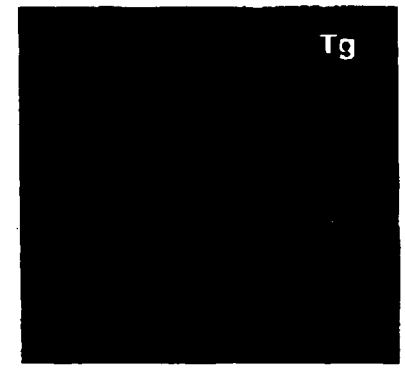
Fig 9d
(1000X)

SEQUENCE LISTING

<160> NUMBER OF SEQ ID NOS: 5

<210> SEQ ID NO 1
<211> LENGTH: 486
<212> TYPE: DNA
<213> ORGANISM: Mouse

<400> SEQUENCE: 1

```
gtcatgcctg atggcttcat aaaggcaggc cagaggccca ggctttctgg gatgccgctt      60
gtcagtgcta accacggggt aacaggtatg cccgtgtctg cttttactgt cattctctct    120
aaagcttacc cagcagtagg tgcccccatc ccatttgatg agattctgta caataggcag    180
cagcattacg acccaagatc tggtatcttt acctgtaaga tcccaggcat atactatttc    240
tcctaccacg tgcatgtgaa agggactcac gtttgggtag gcctgtataa gaacggcacg    300
cctacgatgt acacgtatga tgagtacagc aaaggctacc tggatcaggc ttcagggagt    360
gcaatcatgg agctcacaga aaatgaccag gtatggctcc aattgcccaa tgcagaatca    420
aacggcctct actcctctga gtacgtccac tcgtccttct caggattcct agtggctccc    480
atgtga                                                               486
```

<210> SEQ ID NO 2
<211> LENGTH: 459
<212> TYPE: DNA
<213> ORGANISM: Mouse

-continued

<400> SEQUENCE: 2

```
gtcatgcctg atggcttcat aaaggcaggc cagaggccca ggctttctgg gatgccgctt    60
gtcagtgcta accacggggt aacaggtatg cccgtgtctg cttttactgt cattctctct   120
aaagcttacc cagcagtagg tgcccccatc ccatttgatg agattctgta caataggcag   180
cagcattacg acccaagatc tggtatcttt acctgtaaga tcccaggcat atactatttc   240
tcctaccacg tgcatgtgaa agggactcac gtttgggtag gcctgtataa gaacggcaca   300
cgtatgatga gtacagcaaa ggctacctgg atcaggcttc agggagtgca atcatggagc   360
tcacagaaaa tgaccaggta tggctccaat tgcccaatgc agaatcaaac ggcctctact   420
cctctgagta cgtccactcg tccttctcag gattcctag                          459
```

<210> SEQ ID NO 3
<211> LENGTH: 161
<212> TYPE: PRT
<213> ORGANISM: Mouse

<400> SEQUENCE: 3

Val Met Pro Asp Gly Phe Ile Lys Ala Gly Gln Arg Pro Arg Leu Ser
1               5                   10                  15

Gly Met Pro Leu Val Ser Ala Asn His Gly Val Thr Gly Met Pro Val
            20                  25                  30

Ser Ala Phe Thr Val Ile Leu Ser Lys Ala Tyr Pro Ala Val Gly Ala
        35                  40                  45

Pro Ile Pro Phe Asp Glu Ile Leu Tyr Asn Arg Gln Gln His Tyr Asp
    50                  55                  60

Pro Arg Ser Gly Ile Phe Thr Cys Lys Ile Pro Gly Ile Tyr Tyr Phe
65                  70                  75                  80

Ser Tyr His Val His Val Lys Gly Thr His Val Trp Val Gly Leu Tyr
                85                  90                  95

Lys Asn Gly Thr Pro Thr Met Tyr Thr Tyr Asp Glu Tyr Ser Lys Gly
            100                 105                 110

Tyr Leu Asp Gln Ala Ser Gly Ser Ala Ile Met Glu Leu Thr Glu Asn
        115                 120                 125

Asp Gln Val Trp Leu Gln Leu Pro Asn Ala Glu Ser Asn Gly Leu Tyr
    130                 135                 140

Ser Ser Glu Tyr Val His Ser Ser Phe Ser Gly Phe Leu Val Ala Pro
145                 150                 155                 160

Met

<210> SEQ ID NO 4
<211> LENGTH: 152
<212> TYPE: PRT
<213> ORGANISM: Mouse

<400> SEQUENCE: 4

Val Met Pro Asp Gly Phe Ile Lys Ala Gly Gln Arg Pro Arg Leu Ser
1               5                   10                  15

Gly Met Pro Leu Val Ser Ala Asn His Gly Val Thr Gly Met Pro Val
            20                  25                  30

Ser Ala Phe Thr Val Ile Leu Ser Lys Ala Tyr Pro Ala Val Gly Ala
        35                  40                  45

Pro Ile Pro Phe Asp Glu Ile Leu Tyr Asn Arg Gln Gln His Tyr Asp
    50                  55                  60

-continued

```
Pro Arg Ser Gly Ile Phe Thr Cys Lys Ile Pro Gly Ile Tyr Tyr Phe
65                  70                  75                  80

Ser Tyr His Val His Val Lys Gly Thr His Val Trp Val Gly Leu Tyr
                85                  90                  95

Lys Asn Gly Thr Arg Met Met Ser Thr Ala Lys Ala Thr Trp Ile Arg
            100                 105                 110

Leu Gln Gly Val Gln Ser Trp Ser Ser Gln Lys Met Thr Arg Tyr Gly
        115                 120                 125

Ser Asn Cys Pro Met Gln Asn Gln Thr Ala Ser Thr Pro Leu Ser Thr
        130                 135                 140

Ser Thr Arg Pro Ser Gln Asp Ser
145                 150

<210> SEQ ID NO 5
<211> LENGTH: 152
<212> TYPE: PRT
<213> ORGANISM: Human

<400> SEQUENCE: 5

Val Met Pro Asp Gly Phe Ile Lys Ala Gly Gln Arg Pro Arg Leu Ser
1               5                   10                  15

Gly Met Pro Leu Val Ser Ala Asn His Gly Val Thr Gly Met Pro Val
            20                  25                  30

Ser Ala Phe Thr Val Ile Leu Ser Lys Ala Tyr Pro Ala Val Gly Ala
        35                  40                  45

Pro Ile Pro Phe Asp Glu Ile Leu Tyr Asn Arg Gln Gln His Tyr Asp
        50                  55                  60

Pro Arg Ser Gly Ile Phe Thr Cys Lys Ile Pro Gly Ile Tyr Tyr Phe
65                  70                  75                  80

Ser Tyr His Val His Val Lys Gly Thr His Val Trp Val Gly Leu Tyr
                85                  90                  95

Lys Asn Gly Thr Pro Met Met Asn Thr Pro Lys Ala Thr Trp Ile Arg
            100                 105                 110

Leu Gln Gly Val Pro Ser Ser Ile Ser Gln Lys Met Thr Arg Cys Gly
        115                 120                 125

Ser Ser Phe Pro Met Pro Ser Gln Met Ala Tyr Thr Pro Leu Ser Met
        130                 135                 140

Ser Thr Pro Leu Ser Gln Asp Ser
145                 150
```

DNA ENCODING MUTATED COLLAGEN X

This application is a continuation of and claims the benefit of U.S. application Ser. No. 09/415,551, filed Oct. 8, 1999, now U.S. Pat. No. 6,369,295, issued on Apr. 9, 2002, which claims the benefit of U.S. Provisional Application No. 60/103,550, filed Oct. 8, 1998, the contents of which are incorporated by reference.

Throughout this application, various references are referred to within parentheses. Disclosures of these publications in their entireties are hereby incorporated by reference into this application to more fully describe the state of the art to which this invention pertains.

BACKGROUND OF THE INVENTION

Type X Collagen and its Function

Type X collagen is a homotrimer of three a1(X) chains, with a short (38aa) non-helical amino terminus (NC2), a triple helix of 463aa and a C-terminal highly conserved noncollagenous domain (NC1) of 161aa. This collagen is the major extracellular component synthesized by hypertrophic chondrocytes in growth cartilage destined to be calcified and in zones of secondary ossification (1,2). Expression of the a1(X) collagen gene is specifically associated with hypertrophic chondrocytes and precedes the onset of endochondral ossification (3). Although this collagen does not form fibrils it has been found as fine pericellular filaments in association with cartilage collagen fibrils (4). Type X collagen molecules may also form other supramolecular structures in the matrix, since they have been shown to assemble into a hexagonal lattice in vitro (5).

Apart from association with collagen fibrils, type X collagen interacts with other matrix components, such as annexin V, chondrocalcin (6) and proteoglycans (4). Type X collagen has also been shown to be intimately associated with the calcification process by binding to Ca++ and matrix vesicles which are cell-derived microstructures found in the matrix of calcifying cartilage and bone and thought to be important in the initiation of mineral deposition (7). In addition expression of type X collagen precedes mineral deposition by cultured chondrocytes (8).

Despite the wealth of information about type X collagen, the precise function of this protein and its role in the pathogenesis of chondrodysplasia, has remained the subject of controversy. Because of its specific association with hypertrophic chondrocytes in the calcifying zone of growth plate cartilage, type X collagen has been proposed to be important for endochondral bone formation (2). Proposed functions include, providing an easily resorbed fabric for the deposition of bone matrix during endochondral growth of long bones; providing support as the cartilage matrix is degraded during endochondral ossification (9,10); or regulating the calcification process during endochondral ossification (11–14). Reconciling these opposing views has also been difficult because the consequences of gene mutations which result in type X collagen deficiency in human and mouse differ.

Mutations in the NC1 encoding domain of the human a1(X) collagen gene (COL10A1) have been found to be associated with the autosomal dominant inherited skeletal disorder, Schmid metaphyseal chondrodysplasia (SMCD) (15–18). SMCD is a relatively mild form of metaphyseal chondrodysplasia, resulting from growth plate abnormalities. The SMCD phenotype is variable in severity and characterized by short to normal stature, with genu varum (bow legs), coxa vara (a reduced angle between the femoral neck and shaft) and flaring of the metaphyses of long bone (19,20). Transgenic mice expressing truncated chicken type X collagen, display much more severe skeletal abnormalities, similar to human spondylometaphyseal dysplasia (SMD) (21) in which there is compression of the hypertrophic zone of the growth plate and a decrease in newly formed bony trabeculae.

The phenotypes of SMCD patients and the SMD-like transgenic mice favour a supportive role for type X collagen (15,16,22). Therefore it was surprising to find that mice carrying a null mutation in the al(X) collagen gene (Col10a1) have been reported to show no abnormality and no signs of SMCD (23). K. Cheah in collaboration with others had also created a null mutation in mouse Col10a1 by homologous recombination in ES cells, to gain insight into the function of type X collagen (24). To resolve the apparently contradictory consequences of mutations in the gene in human and mouse and gain better insight into the pathogenesis of SMCD, we focused our study on the consequences of type X collagen deficiency on the structure of the growth plate and trabecular bone, and on the organization of matrix components within cartilage.

This disclosure showed that type X collagen deficiency in mice does have phenotypic consequences which partly resemble SMCD, reducing the apparent discrepancy in phenotype between human and mouse (24). Intriguingly, the major impact of type X collagen deficiency does not lie in its site of expression, the hypertrophic zone, but rather affects other zones of the growth plate and in bone. It is also found that the consequence of loss of type X collagen in mutant mice is a major change in the distribution of matrix materials such as proteoglycans and matrix vesicles, within the epiphyseal cartilage. Other features of type X collagen deficiency are a significant compression of the resting zone and articular cartilage.

Phenotypic features which partly resemble SMCD were found, such as persistence of cartilage in trabecular bone, alterations in bone mineralization and trabecular structure. In particular, type X collagen deficient mice develop coxa vara, one of phenotypic changes common in human SMCD. These findings have led us to propose a function for type X collagen. Based on these findings we propose that type X collagen plays a role in the normal compartmentalization of the cartilage matrix. Type X collagen deficiency alters the distribution of cartilage matrix components thereby impacting on the supporting properties of the growth plate and the mineralization process, resulting in abnormal trabecular bone. This hypothesis would accommodate the previously conflicting views of the function of type X collagen and of the molecular pathogenesis of SMCD.

SUMMARY OF THE INVENTION

This invention provides an isolated DNA comprising the sequence which codes for a mutated collagen X or a portion thereof wherein the expression of said DNA regulates bone growth. In an embodiment, the DNA comprises the sequence of Col10-13del as set forth in FIG. 2. This invention also provides a vector which comprises the above-described DNA.

This invention also provides a method for production of the a polypeptide which regulates bone growth comprising a host-vector system which comprise the above vector and an appropriate host.

This invention provides a polypeptide encoded by the isolated DNA comprising the sequence which codes for a mutated collagen X or a portion thereof wherein the expression of said DNA regulates bone growth. This invention also provides a polypeptide which comprise the portion of the mutated collagen X capable of regulating bone growth.

This invention provides a composition comprising the above polypeptide and a suitable carrier. This invention provides a pharmaceutical composition for increasing bone growth comprising the above polypeptide and a pharmaceutically acceptable carrier.

This invention also provides a method of treating a subject afflicted with dwarfism comprising administering to the subject an amount of the polypeptide comprising a portion of the mutated collagen X capable of regulating bone growth or the isolated DNA comprising the sequence which codes for a mutated collagen X or a portion thereof wherein the expression of said DNA regulates bone growth effective to reverse the dwarfism.

This invention provides a method of treating a subject afflicted with low bone mass comprising administering to the subject an amount of the polypeptide comprising a portion of the mutated collagen X capable of regulating bone growth or the isolated DNA comprising the sequence which codes for a mutated collagen X or a portion thereof wherein the expression of said DNA regulates bone growth effective to treat low bone mass in the subject.

This invention provides a method of improving the quality and speed of bone union after fracture in a subject comprising administering to the subject an amount of the polypeptide comprising a portion of the mutated collagen X capable of regulating bone growth or the isolated DNA comprising the sequence which codes for a mutated collagen X or a portion thereof wherein the expression of said DNA regulates bone growth effective to improve the quality and speed of bone union.

This invention further provides a transgenic animal comprising an isolated DNA comprising the sequence which codes for a mutated collagen X or a portion thereof wherein the expression of said DNA regulates bone growth.

BRIEF DESCRIPTION OF THE FIGURES

FIG. 2. Comparison of the mouse and human nonsense sequence generated from an equivalent 13 base pairs deletion within the NC1 domain of collagen X. Amino acids are numbered from the start of translation (3). The underlined bases in the wt sequence (SEQ ID NO: 1) represent the 13 bp deleted in the mutant sequence (SEQ ID NO: 2). Variations between the mouse and human nonsense sequences are highlighted in bold. The boxed amino acids represent a mutant specific polypeptide synthesized for polyclonal antibody production in rabbit. The nonsense amino acid sequences resulting from the deletion in the mouse and human are aligned for comparison. Amino acids are numbered form the start of translation(3). The underlined bases in the wt sequence represent the 13 bp deleted in the mutant sequence. Variations between the mouse and human nonsense sequences are highlighted in yellow. The boxed amino acids represent a mutant specific polypeptide synthesized for polyclonal antibody production in rabbit. Wild type amino acid sequence (SEQ ID NO: 3). Mutant mouse amino acid sequence (SEQ ID NO: 4). Mutant human amino acid sequence (SEQ ID NO: 5).

FIG. 4. X-ray images of 5 week old Col10-13del mice compared to non-transgenic mice. Note marked hyperostosis of bones as indicated by the increased opacity (whiteness) of image. A–B. 34.10.372(NT) and 34.10.373(Tg) top views. C–D 34.10.372 and 34.10.373 lateral view.

FIG. 5. X-rays of 10 week old Col10-13del mice compared to non-transgenic mice. A–B 34.10.57(NT) and 34.10.54(Tg) top views. C–D 34.10.57 and 34.10.54 lateral view.

FIG. 6. X-rays of 15 week old Col10-13del mice compared to non-trangenic mice. A–B. 34.10.57(NT) and 34.10.54(Tg) top views. C–D 34.10.57 and 34.10.54 lateral view.

FIG. 9. Expression of wild type and mutant collagen X. Immunofluorescence (FITC staining) on cryosections from new born distal femur growth plates of Col10-13del transgenic (tg, a,c,d) and non-transgenic mice (nt,b). a,b) ColX antibody staining; c) 13-del mutant protein antibody staining. Note punctate staining in the 13 del antibody stained section from transgenic growth plat, indicating mainly intracellular staining of hypertrophic chondrocytes (c) compared to extracellular staining with collagen X antibody staining of non-transgenic sections (b). In non-transgenic sections, only very weak background was seen (not shown). d) Immunostaining showing intracellular localisation of the Col10-13del protein in osteoblast-like cells found in the trabecular bone in (c). T: trabecular bone H: hypertophic zone.

DETAILED DESCRIPTION OF THE INVENTION

Figure 1:
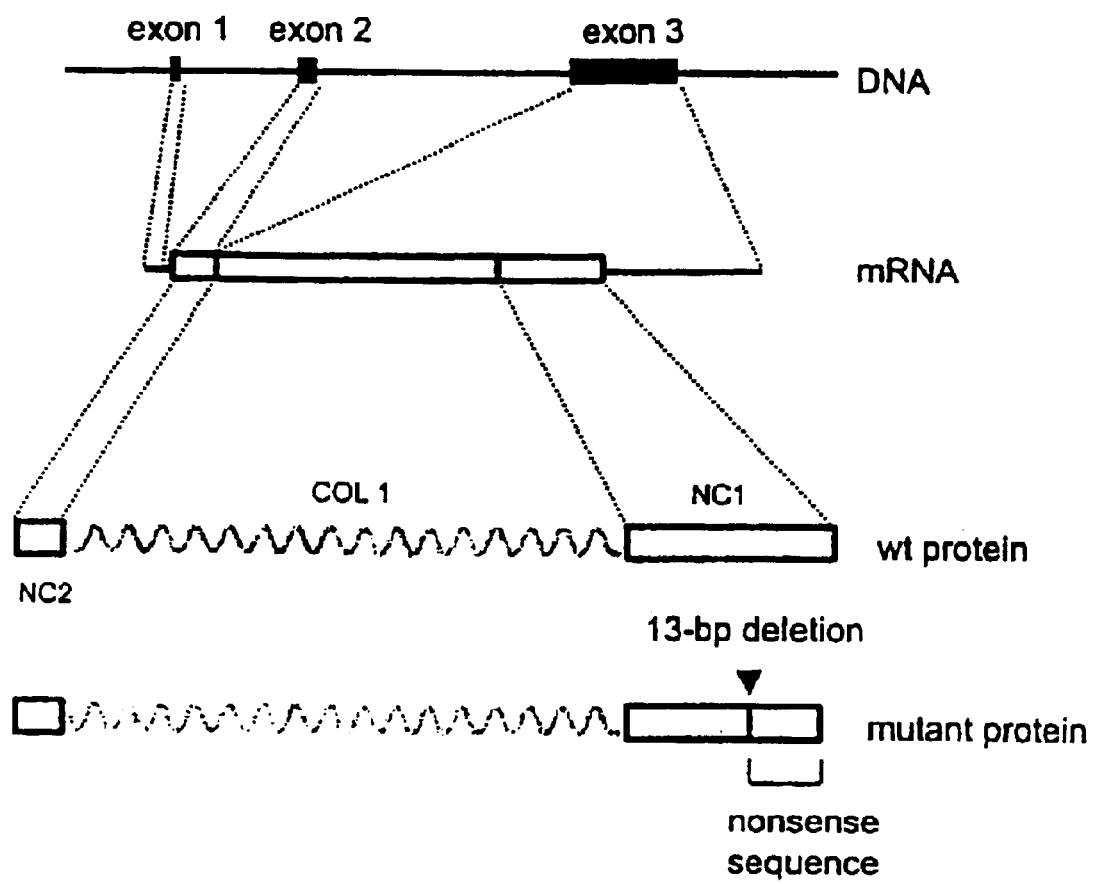
FIG. 1. Diagram showing the structure of the Col10-13del transgene. Collagen X gene and protein structure.

This invention provides an isolated DNA comprising the sequence which codes for a mutated collagen X or a portion thereof wherein the expression of said DNA regulates bone growth. It is the intention of this invention to cover all mutant collagen X which is capable to regulate bone growth. This Invention also covers portion of mutated collagen X which has the biological activities of regulating bone growth and polypeptides which bears this domain (portion).

This invention provides an isolated DNA comprising the sequence Col10-13del as set forth in FIG. 2 or a portion thereof of which regulates bone growth when expressed.

This invention also provides a vector which comprises the above-described DNA.

Vectors which comprise the isolated nucleic acid molecule described hereinabove also are provided. Suitable vectors comprise, but are not limited to, a plasmid or a virus. These vectors may be transformed into a suitable host cell to form a host cell vector system for the production of a polypeptide capable of regulating bone growth.

This invention further provides an isolated DNA or cDNA molecule described hereinabove wherein the host cell is prokaryote or eukaryote. For example, the cells may be bacterial cells (such as E.coli), yeast cells, fungal cells, insect cells or animal cells. Suitable animal cells include, but are not limited to Vero cells, HeLa cells, Cos cells, CV1 cells and various primary mammalian cells.

This invention also provides a polypeptide encoded by above-described DNA. This invention also provides polypeptide which bears the domain(s) of the mutant collagen X which regulates bone growth.

This invention also provide a composition comprising the above-described polypeptide and a suitable carrier. A suitable carrier are carrier which is capable of dissolving the polypeptide and yet not affect the biological activity of said polypeptide. For example, the carrier may be a physiologically saline.

This invention also provides a pharmaceutical composition for increasing bone growth comprising the above-described polypeptide and a pharmaceutically acceptable carrier.

For the purposes of this invention "pharmaceutically acceptable carriers" means any of the standard pharmaceutical carriers. Examples of suitable carriers are well known in the art and may include, but not limited to, any of the standard pharmaceutical carriers such as physiologic saline solution, phosphate buffered saline solutions, phosphate buffered saline containing Polysorb 80, water, emulsions such as oil/water emulsion, and various type of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

This invention also provides a method of treating a subject afflicted with dwarfism comprising administering to the subject an amount of the above polypeptide or the above-described DNA of effective to reverse the dwarfism.

Methods of determining an "effective amount" are well known to those skilled in the art and depend upon factors including, but not limited to: the size of the patient and the carrier used.

This invention provides a method of treating a subject afflicted with low bone mass, including but not limited to osteoporosis, comprising administering to the subject an amount of the above polypeptide or DNA via for example the administration of bone marrow/stromal cells carrying and expressing the Col10-13del transgene.

This invention provides a method of enhancing the quality of fracture healing and of the healed bone of a subject comprising administering to or implanting into or around the bone of the subject an amount of the above polypeptide or DNA comprising the above-described DNA effective to enhance the quality of fracture healing and of the healed bone.

As used herein, enhancing the quality of fracture healing means an increase in the rate of callus and bone formation, a reduction in the incidence of failure to heal (non-union), an increase in the quantity of bone formed, or an improvement in the mechanical properties of the callus or of the bone formed. Enhancement of the healed bone means an improvement in the mechanical properties of the bone or and increase in the quantity of bone formed.

This invention also provides to a patient with low bone mass to improve the quality of the healed bone. Since type X collagen protein is an extracellular matrix component, it and its mutant forms may be administered extracellularly via local therapy which involves biodegradable vehicles. Methods of administering the polypeptide includes implanting coated or impregnated forms of solid support material e.g. ceramic powders (Gordon, E., Lasserre, A, Stull, P., Bajpai, P. K., England, B. 1997 Biomed Sci Instrum 33: 131–136); polymethymethacrylate cement; biodegradable polymers (such as poly lactides-co-glycolides Ramchandani M. Robinson, D. 1998 J. Controlled Release 54: 167–175), collagen vehicles such as resorbable collagen membranes (King, G. N., King, N., Hughes, F. J. 1998. J. Periodontal Res 33: 226–236) or gels impregnated with extracellular matrix proteins and the polypeptide and other similar approaches.

Methods of allowing site-specific gene delivery of the DNA may include implanting osteoblasts which have been transfected with the Col10-13del transgene and which express the transgene. We have previously identified a subset of the regulatory sequences in the Col10a1 gene (within the whole col10-13del construct) which can direct expression specifically to endosteal cells and osteoblasts (Cheah and Poon, unpublished results). Alternatively, implants containing chondrocytes transfected with the Col10-13del construct and expressing the transgene may be transferred to bone defects. Liposome based vehicles may also be used as a means to deliver the Col10-13del transgene to cells at the fracture site.

In an embodiment, the above-described DNA is operatively linked to inducible regulatory element.

This invention further provides a transgenic animal comprising an the isolated DNA comprising the sequence Col10-13del as set forth in FIG. 2 or a portion thereof of which regulates bone growth when expressed.

In an embodiment, the transgenic animal of claim is a mouse.

This invention also provides a transgenic animal comprising an DNA designated Col10-13del as set forth in FIG. 2.

This invention provides a method for identifying whether an agent which stimulates bone growth comprising steps of:
a) administering the agent to the above transgenic animal; and b) examining the transgenic animal after the administration of the agent to determine whether bone growth has been stimulated.

This invention also provides a method for assessing the effect of surgery on increasing bone length comprising steps of: a) performing surgery on the above transgenic animal; and b) assessing the increase in bone length of the animal to determine the effect of surgery on said animal.

In an embodiment, the assessment is performed by direct measurement of the increase in bone length and the animal is sacrificed at different time for the accurate measurement.

The invention also provides a method for assessing the effect of bone growth stimulating agents on fracture repair comprising steps of: a) creating a fracture repair in the above-described transgenic animal; b) administering the agent to the transgenic animal; and b) examining the transgenic animal after the administration of the agent to determine whether bone growth has been stimulated.

This invention will be better understood from the Experimental Details which follow. However, one skilled in the art will readily appreciate that the specific methods and results discussed are merely illustrative of the invention as described more fully in the claims which follow thereafter.

Experimental Details

Molecular Mechanisms Underlying SMCD Type X Collagen Mutations in Humans

An important issue raised by our findings, is the relative mildness of phenotype in the null mutants compared with the SMD-like transgenic mice and human SMCD (reviewed in 25). Since collagen a chains associate via the NC1 domain, it has been proposed that in human SMCD, the NC1 mutations result in failure of trimer assembly (15,16) and the phenotypic changes are caused because type X collagen is depleted in the matrix. This proposal is supported by recent reports that collagen al(X) chains carrying SMCD mutations are unable to form trimers in in vitro assembly and cell transfection experiments (26, 27). In the SMD transgenic mice, the chondrodysplasia is postulated to be caused by a depletion of type X collagen as a result of instability/degradation of mutant chicken-mouse hybrid protein (21) or because the chicken a chains interfere with the normal assembly of mouse type X collagen. The ability of a1(X) chains with internal deletions within the helix to assemble with normal chains as heterotrimers and be secreted, support the latter explanation (27). It is notable that the changes in trabecular structure observed in SMD-like transgenic mice (21) were similar but more severe than in the type X collagen null mutants. Our results suggested that different phenotypes of the null mutants and the SMD-like transgenic mice probably reflect differing severity of outcome of mutations resulting in loss versus gain of function.

The reason for the late onset of coxa vara and the relatively milder phenotypic changes in type X collagen mutant mice, compared with human SMCD, is still not fully understood. The late onset of the defect in the mutant mice compared with the SMCD patients may be related to the differences in loading of the growth plate between man, a biped and mouse, a quadriped. However, the type X collagen content in SMCD growth plates has not been determined. In addition it is not known if synthesizing abnormal a1(X) collagen chains which cannot assemble, has additional effects on hypertrophic chondrocytes, affecting their growth. It would therefore be important to compare the phenotypic consequences of the null with a SMCD mutation in mice.

Experimental Results & Discussion

Expressing Type X Collagen Chains Containing a SMCD Mutation in Transgenic Mice

We have identified genomic sequences in the 5' flanking region, first and second introns of the mouse Col10a1 gene which were sufficient to drive tissue-specific expression of a FLAG- epitope-marked form of collagen X in hypertrophic chondrocytes in transgenic mice. There was also some expression in some chondrocytes in the lower proliferative zone. Expression was also seen in a few cells in the bone marrow compartment which could be osteoblasts. We used these sequences to initiate experiments designed to address these questions and have started to study the phenotypic consequence of expressing collagen a1(X) chains carrying a SMCD mutation in hypertrophic chondrocytes of mice heterozygous and homozygous null for type X collagen.

Figure 3:
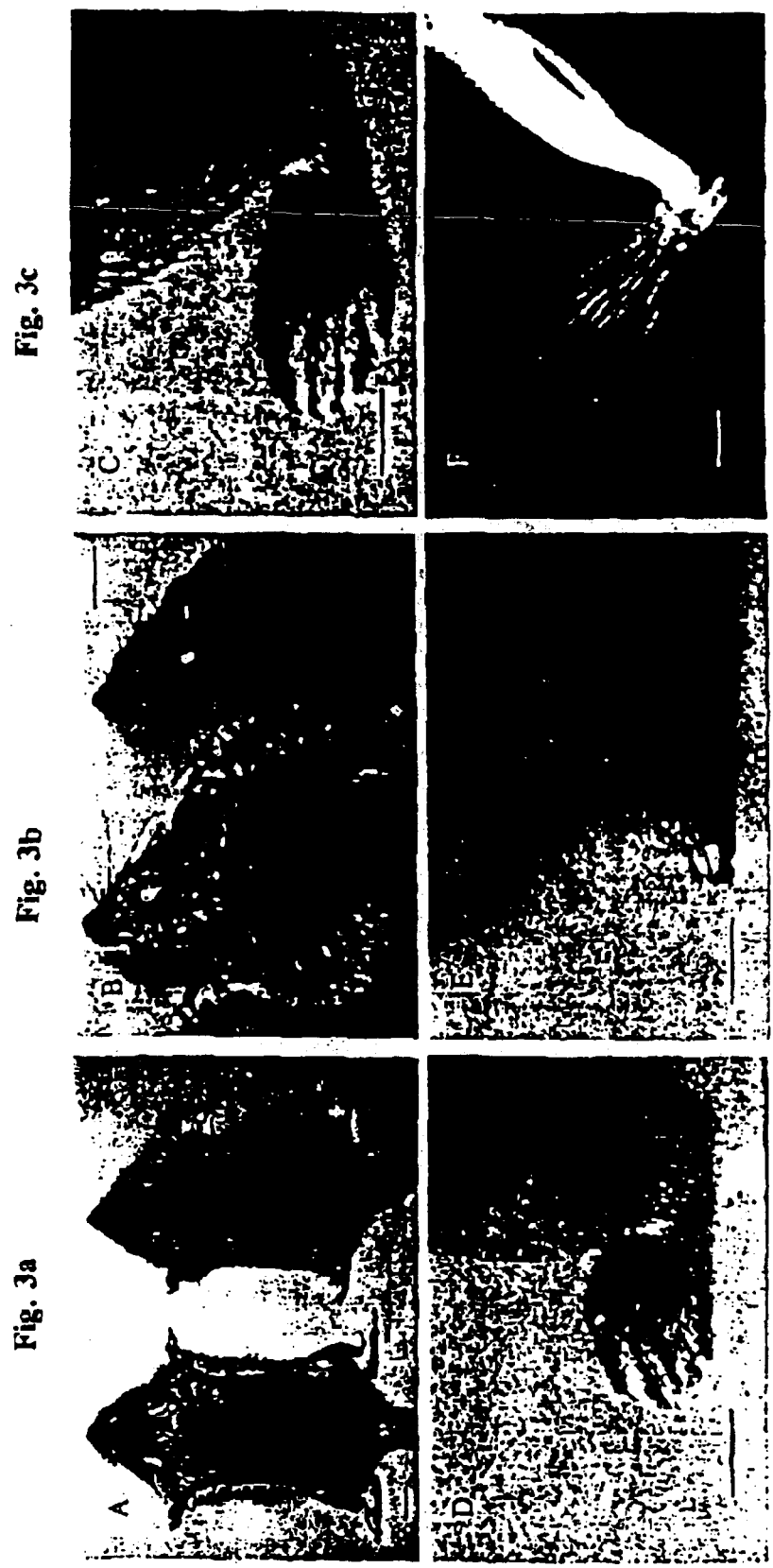
FIG. 3. Pictures of 6 month old Col10-13del transgenic (Tg) and non-transgenic (NT) mice and X-rays. X-rays shown here and in subsequent figures are taken at the same exposures using a mammogram machine. A and B the scale bar represents 1 cm; C–E scale bar represents 0.5 cm. A. Left 34.10.57(NT), right 34.10.54 (Tg) at 6 months of age showing differences in overall body length and shape, in Particular differences in the length of the limbs. B. Left 34.10.57(NT), right 34.10.224(Tg) at 6 months, showing differences in the shape of the head. C–E. 34.10.372 (NT), 34.10.373 (Tg) and 34.10.224 (Tg) respectively. Demonstrates the variability in severity of the malformation of the feet and digits. E also has an extra digit. F. X-ray of 34.10.224, showing the presence of an extra digit.

Sited-directed mutagenesis (15) is used to introduce the mutation into a genomic clone containing the whole mouse collagen X gene (Col10a1) and the resulting clone is designated Col10-13del. The mutation was a 13-bp deletion within the conserved NC1 domain (FIG. 1). This mutation causes a shift in the amino acid reading frame at position 619 resulting in the production of a nonsense sequence (52 amino acids) from residue 620 with a prediction premature termination at 671, 9 amino acids shorter than the wild type (FIG. 2). This mutant construct, Col10-13del was introduced into the germ-line of mice wild-type or heterozygous for Col10a1, by transgenesis. Three transgenic mouse lines carrying this transgene on a wild-type Col10a1 genetic background were found to have abnormal skeletal phenotype which, although variable in severity, was very similar in these lines. All three of these lines expressed the transgene as assessed by RT-PCR on RNAs from cartilage of the mice. Surprisingly the external gross phenotype of these transgenic mice was not similar to human SMCD but rather resembled other human skeletal disorders as follows:

Gross Phenotype:

The phenotype observed in the Col10-13del mice appeared to be a rhizomelic skeletal dysplasia with analogy to human cranio-tubular remodelling disorders. The onset of observable differences in phenotype between transgenic and wild-type mice occurs 4–6 days post-partum. The transgenic mice are smaller than their littermates. The observed phenotype at this stage involves she distal digits. The digits are shorter and fatter than their wild type counterparts and appear to be hypermobile (FIG. 3). There is variation in degree in which the digits are short, bent or curved outwards, but this is a common feature of all the transgenic mice. Fore- and hind-limbs are affected, often the latter more severely. As the mice develop, a rounding of the fronto-nasal area becomes apparent. X-ray analysis of the mice from 5 weeks (5,10,15 wks) onwards has revealed a progressive hyperostosis (hyper=3D increased, ost=3D bone, osis=3D condition i.e. a condition of increased bone), which affects skull, ribs, spine and long bones (FIGS. 4–6). As with the distal digits the long bones (humeri and femurs), ribs and pelvic elements are also shorter and broader than those observed in the wild type mice. There is also a strange lucency and expansion of the medullary cavity distal to the mid-point of the femurs. By 10–15 weeks the mice show varying degrees of waddling gait with splayed feet, with those most severely affected showing a "dragging posture" of their rear end probably because the hind legs are not normally flexed.

Figure 7:
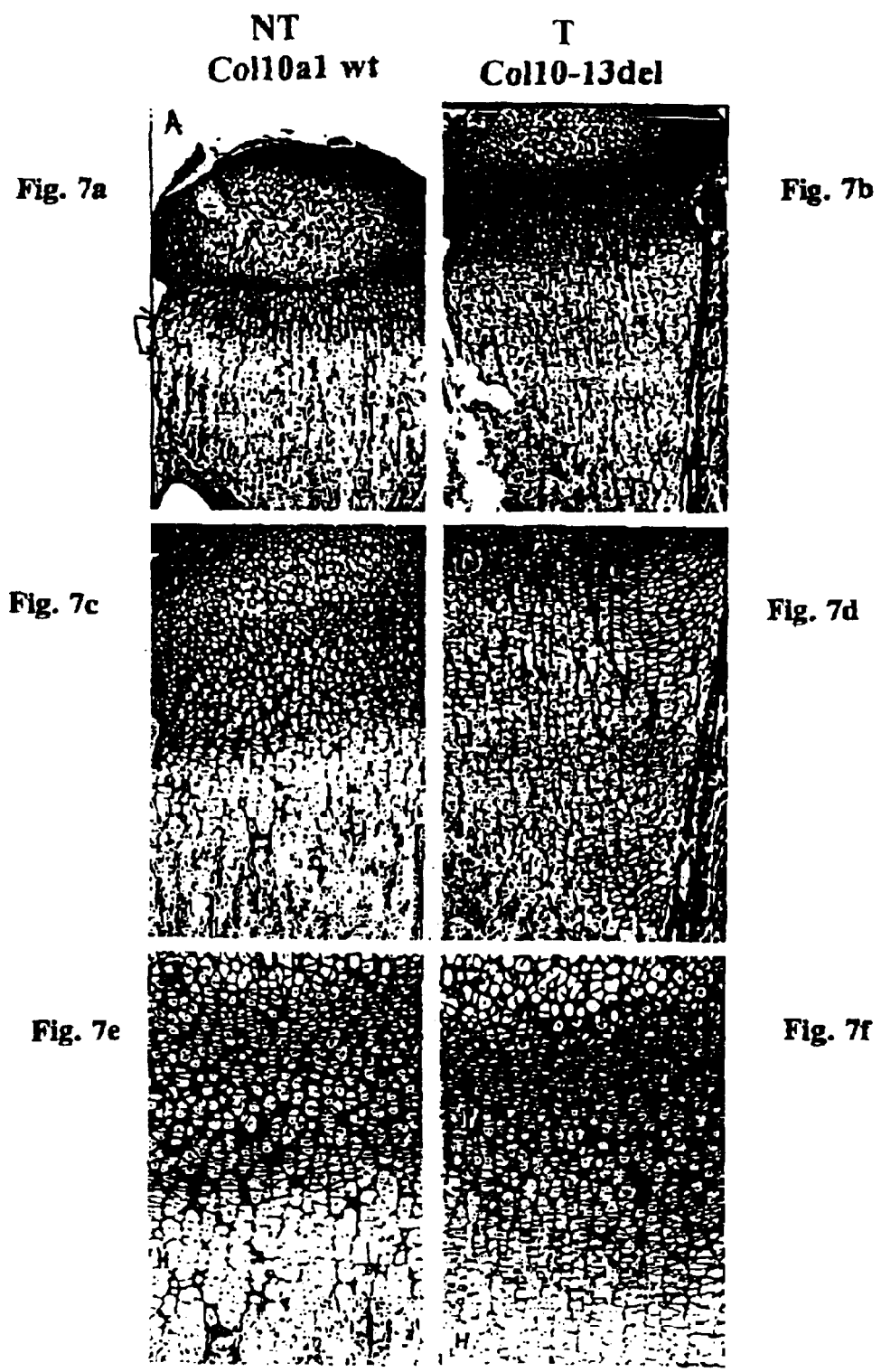
FIG. 7. Histology of growth plates of Col10-31del and wild-type littermate. A, C, E are wild-type non-transgenic (NT); B, D, F are Col10-13del transgenic (T). Note the greatly increased heights of the proliferating (p) and hypertrophic (h) zones in the Col10-13del mice as compared to wild-type littermate.
Figure 8:
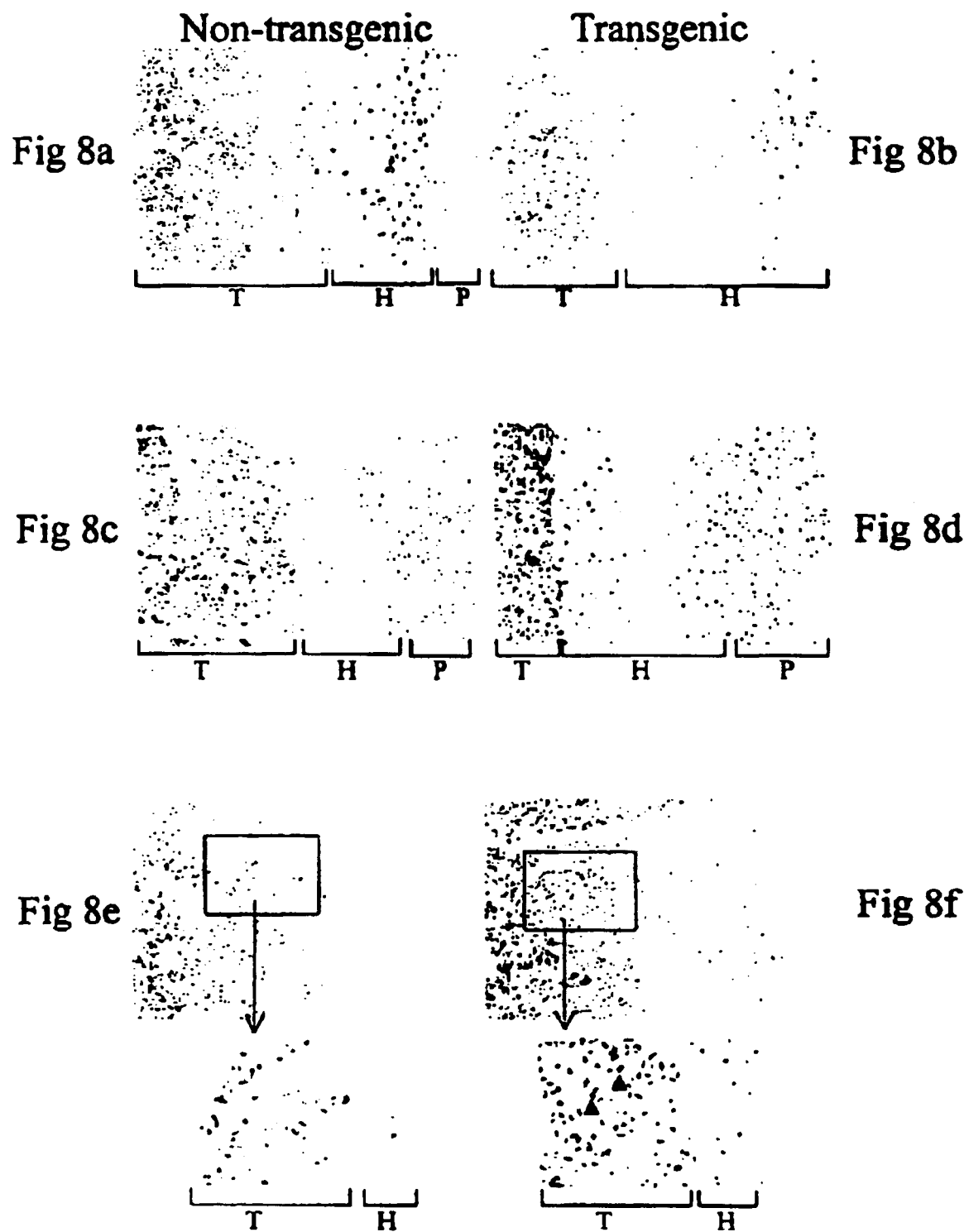
FIG. 8. Expression of p57kip2, PCNA and Hsp47 in 2 days post partum distal femur growth plates of Col10-13del transgenic and non-transgenic mice. Expression shown are: a,b) cyclin-dependent kinase inhibitor p57kip2; c,d) proliferating cell nuclear antigen (PCNA, antibody from Santa Cruz Biotechnology, Santa Cruz, Calif.); e,f) heat shock protein 47 (Hsp47). Positive signal in cells is shown by the brown immunoperoxidase staining using Vectastain ABC kit (Vector Laboratories, Burlingame, Calif.). Staining of trabecular bony matrix is non-specific. All images are at 100× magnification except boxes are regions magnified 200 times. T: trabecular bone, H: hypertophic zone. P: proliferative zone.

Histopathology:

Comparison of the histology of sections from the growth plates of 10 day and 4 week non-transgenic and Col10-13del mice show marked differences (FIG. 7). The proliferative zone of transgenic mice is enlarged compared to non-transgenic littermates. The most dramatic changes are seen in the hypertrophic zone which is considerably increased in height in Col10-13del mice, with hypertrophic chondrocytes appearing disorganized and reduced in size. In addition, the trabeculae at the chrondro-osseuts region in mutants appeared increased in size (FIG. 7).

Ultrastructure:

ultrastructural changes in the growth plates of the Col10-13del mice were analyzed. Initial analyses of 10 day neonates show that the matrix organization in the transgenic mice within the proliferating zone is such that a distinct pericellular matrix compartment is missing, whereas in the non-transgenic it is present. In the hypertrophic zone this compartment is present in both groups. The density of organelles within the cell cytoplasm (rough endoplasmatic reticulum, Golgi, mitochondria, etc.) within the cells of transgenic mice is in the proliferating zone significantly reduced, whereas in the non-transgenic proliferating cells it is of a normal density. In the hypertrophic zones this value is much more difficult to assess; however, in the transgenic mice we identified an increased density of extended and filled endoplasmatic reticulum membrane cepterns, which are not present in non-transgenic mice. The significance of these findings will need further analyses. However it is possible that it may be that the ultrastructural changes are the result of two effects: in the proliferating zone, which lacks type X collagen, ectopic expression of the col10-13del transgene causes interference/alteration in matrix assembly and affects chondrocyte proliferation. In the hypertrophic zone where the normal type X collagen is also present, mutant-wild-type heterotrimers may be forming which are difficult to secrete or are targeted for degradation, causing distension of the ER.

Molecular Bases of the Growth Plate and Bone Abnormalities

The occurrence of hyperostosis in these mice is an interesting phenomenon, especially since type X collagen is not normally synthesized in bone. There is however some evidence that residual collagen X is present in the cartilaginous remnants within bone trabeculae (24). There are several possible underlying causes, which singly or in combination, may underlie the abnormal bone phenotype in these mice:

a. In both the human and mouse collagen X, the mutation results in a similar nonsense amino acid sequence terminating at the same residue. However, 15 of the 52 nonsense amino acids are different between the mouse and human sequence (FIG. 2). This represents 29% variation and it is possible that the altered peptide sequence may contribute towards the phenotypic changes for example behaving as a signalling molecule/growth factor.
b. The phenotypic changes could be the result of ectopic expression of the transgene in the lower proliferative zone and/or osteoblasts
c. Synthesis of abnormal collagen X molecules which form heterotrimers with wild type chains
d. The phenotype is caused by the increased degradation of mutant molecules by the hypertrophic chondrocytes.
e. Since collagen X has been shown to have a strong affinity for proteoglycans, the bone overgrowth could be caused by an imbalance in the matrix components, especially proteoglycans. This alteration in proteoglycan deposition or biosynthesis could contribute to the bone overgrowth since these molecules have been shown to be important for bone growth and remodelling.
f. The consequence of expressing abnormal collagen X could be to disrupt its interaction intracellularly with chaperones and extracellularly with other matrix molecules, proteinases and/or receptors (e.g integrins). These altered interactions are likely to alter intracellular signal transduction and hence chondrocyte proliferation and/or differentiation. The impact of such alterations are likely to be mostly at the chondro-osseous junction.

Further Experimentation:
A. Basic Studies

Studying the molecular basis of the abnormalities in these mice will help us to understand the relationship between genotype and phenotype and will contribute to a further definition of the role of type X collagen in the formation and structural integrity of growth cartilage. This insight will be extremely valuable for an understanding of the pathology of diseases which result in the degeneration of cartilage, such as osteoarthritis. The progressive increase in bone density in these mice also imply deregulation of bone growth and remodelling. It is not yet clear if the phenotypic abnormalities are a primary or secondary effect of expression of the Col10-13del transgene. However this abnormality raises many questions about the regulatory pathways for bone growth. Therefore these mice will be used to:

a) identify key molecules and pathways important for the regulation of bone growth, with implications for human bone disorders.
b) study differentiation, proliferation, apoptosis and cell-cycle regulation in the growth plate.
c) study the role of the marrow microenvironment and the chondro-osseous junction on hematopoiesis, vascularization of bone, bone formation and remodelling.

The Following Studies Will be Performed:
i) Phenotype and Molecular Characterization Cartilage, the growth plate and membranous bone of mutants will be extensively analyzed. The spatial and temporal expression pattern of the transgene during development and postnatal growth these mice will be studied further by insitu hybridization and immunohistochemistry. In situ hybridization analyses will be used to determine if the transgene is expressed at the appropriate time in development as the wild type gene. Specific oligonucleotide or riboprobes will be generated spanning the deletion site. Conditions of hybridization will be optimized to give specific hybridization only to the transgene mRNA. In addition since our previous studies with the wild type gene marked by a FLAG epitope had shown expression in the hypertrophic chondrocytes as well as some proliferating chondrocytes. In situ hybridization using wild type Col10a1 probe will show the overall distribution of both mutant and normal transcripts and assess if the Col10-13del transgene shows similar ectopic expression. Since the 13bp deletion creates a new peptide sequence in the NC1 domain, antibodies can be raised against the altered peptide and used for immunohistochemistry. This will enable us to determine the localization of the mutant collagen X protein. Attention will also be taken to determine if mutant protein is present in the bone in the cartilaginous remnants within boney trabeculae.

Levels of expression of the mutant transcript relative to wild-type will be determined using RNAse protection assays using a riboprobe spanning the mutation, enabling both type of transcripts to be detected in one assay.

Proper chondrocyte differentiation will be assessed using appropriate molecular markers (30, 31), including type IIA procollagen (marker for pre-chondrocytes); long-form Col9a1, Col11a2, aggrecan (expressed by proliferating and mature chondrocytes); link protein, indian hedgehog (proliferating chondrocytes); PTH-PTHrP receptor (marks chondrocytes at the boundary between the proliferative and hypertrophic zones); and Col10a1 (marks hypertrophic chondrocytes); BMP-6, FGFR3 (marks all chondrocytes). In situ hybridization studies to analyse the biochemical consequences of expressing the transgene at developmental stages 14.5, 16.5 dpc; and postnatal stages: newborn, 5dpp, 5, 10, 15 wks will be performed.

To study possible secondary impact of abnormal bone formation in Col10-13del mutant mice on hematopoiesis we will analyse the long bones in situ for deviations from normal with respect to the morphological appearance of the stroma and haematopoietic cells, incidence of apoptotic and cycling cells and marrow cell number and composition. For this assessment specific molecular markers will be used in situ hybridization studies such as for osteoblasts (Osf2, osteocalcin), osteoclasts (acp5, encoding tartrate resistant acid phosphatase, CSF-1, GM-CSF); chemokines essential for initiation of bone marrow haematopoesis in ontogeny (e.g. SDF-1); metalloproteinases (BP-1, MMPs) and haematopoietic cytokines (e.g. IL-6, G-CSF) and others.

ii) Further Control Studies

The following experiments will be performed to determine if the abnormal phenotype is the consequence of:

a) ectopic expression of the transgene
b) truncated NC1 domain in collagen X molecules caused by the 13 bp del
c) the novel mutant peptide sequence caused by the 13 bp del which differs from the human
d) The formation and/or processing and/or matrix deposition of collagen X heterotrimers consisting of mutant and wild-type chains.

To address a) above, transgenic mice will be generated carrying normal Col10a1 sequences with the same regulatory elements as in the Col10-13del construct. The phenotype of mice expressing such a transgene will be compared with that of the Col10-13del mice. The expression pattern of the transgene can be monitored by introducing an internal ribosome entry site sequence followed by an ATG and green fluorescent protein (GFP), at a position downstream of the Col10a1 translational stop but upstream of the polyA attachment signal.

Alternatively, mice carrying the col10-13del mutation will be generated using homologous recombination in ES cells to "knock-in" the mutation (Ramires-Solis, R. & Bradley, A Curr. Opin. Biotechnol. 5, 528–533 (1994); Baudoin, C., Goumans, M. -J., Mummery, C. & Sonnenberg. A. Genes & Development 12, 1202–1216).

To address b) a construct containing a SMCD point mutation which results in a premature stop codon in the NC1 domain has been made. This construct will be used to generate transgenic mice and the phenotype of these mice compared with the Col10-13del mice.

To address c) transgenic mice (Col10-13delH) will be made carrying the same 13 bp deletion mutation except that the downstream amino sequence following the 13 bp deletion is identical to that in human SMCD mutation. The phenotype of this mouse will be compared with the original Col10-13del mouse.

To address d) transgene mice (Col10-13del) will be generated on varying genetic backgrounds: heterozygous and homozygous null for Col10a1. The phenotypes of these mice will be compared with the mice described here, which are Col10-13del on a wild-type Col10a1 background. In addition, the biosynthesis and processing of collagen X in chondrocytes isolated from mutant mice will be analyzed.

iii) Studying the Role of Proteoglycans (PGs) and Glycosaminoglycans (GAGs) in Regulating Bone Growth.

In a recent report, EXT1, a transmembrane glycoprotein present in the ER has been shown to be critical for the expression of cell surface glycosaminoglycans (GAGs) Mutations in EXT1 is the cause of hereditary multiple exostosis (HME), an inherited skeletal disorder characterized by skeletal malformation due to excessive bone growth (32). Type X collagen has been shown to have a strong affinity to bind to proteoglycans (PGs). We propose to test the possibility that the abnormal type X collagen associates differently or fails to associate with proteoglycans (PGs) and/or GAGs in the Col10-13del mice, thereby causing the bone overgrowth. The biosynthesis of GAGs and PGs will be studied and compared in explant cultures of growth plates from non-transgenic and transgenic mice. In addition the Col10-13del construct will be transfected into hypertrophic chonrocytes and the effect on PG and GAG biosynthesis studied. These experiments will enable us to determine if PG metabolism has been affected by the abnormal type X collagen.

iv) Cell Proliferation and Cell Cycle Regulation in Col10-13del Hypertrophic Chondrocytes Cell proliferation is controlled by a complicated network of extracellular and intracellular signalling pathways that process growth regulatory signals and integrate them into the basic cell-cycle regulatory machinery through the control of the cyclin-dependant kinases (CDKs). CDKs are regulated by cyclins (positive regulation) and CDK inhibitory proteins CKIs (negative regulation). Recently it has been shown that mice lacking the CDK inhibitor p57kip2 show abnormal proliferation of hypertrophic chondrocytes and abnormal endochondral ossification (33,34). The proliferative ability of the hypertrophic chondrocytes by PCNA (proliferating cell nuclear antigen) immunostaining or BrdU labelling will be studies and compared. In addition TUNEL (TdT-mediated dUTP-X nick end labelling assay, Boehringer Mannheim Ltd) assays will be performed to assess the degree of apoptosis in the transgenic growth plate compared to non transgenic littermates. Furthermore, PCR differential display will be used to compare the expression profiles of wild-type and transgenic growth plates and to clone out genes which are up-regulated or down-regulated. These studies will identify key regulators of bone and cartilage growth and the signal transduction pathways which are affected in the Col10-13del mice and molecular interactions at the cartilage-bone junction.

These studies also have implications for understanding the mechanisms underlying the development of bone and cartilage tumors. Such cartilage and bone tumors include but are not limited to metastatic bone tumors with primary tumor arising from the breast and prostate, osteoid osteoma, osteochondroma, chondroma, osteoblastoma, osteogenic sarcoma, chondrosarcoma, fibrosarcoma or any other tumors in which increase cartilage and/or bone formation occurs. In addition, these studies will also have implications for understanding the mechanism underlying diseases caused by overgrowth or remodelling problems of bone such as for hyperostosis, exostoses and osteopetrosis, etc.

v) Remodeling and Turnover of Cartilage and Bone

The effect of the 13del mutation on the degradation of collagen X will be assessed. To assess degradation of the mutant type X collagen in growth plate, we will isolate the type X collagen substrate from the growth plates of transgenic and wild-type mice (Chan, Azsodi, Fassler and Bateman, unpublished data). Intact and papsinised collagen X will be purified by selective salt fractionation and by affinity chromatography using Sephacryl S-500 resins. This will provide chemical amounts of intact type X collagen (59 kDa) containing both NC1 and NC2 domains as well as pepsined (45 kDa with the NC1 and NC2 domains removed) for metalloproteinase (MMP) cleavage anaylysis. This will provide data on the susceptibility of the mutant collagen to MMP cleavage. N-terminal amino acid sequencing will be performed on products with major or significant MMP cleavage, MMP cleavage products resolved by SDS-polyacrylamide gel electrophoresis will be sequenced directly following transfer onto PVDF membranes.

vi) Bioinformatics and Structural Analyses

Interspecies comparisons of genes and identification of homologues in vertebrates and invertebrates can reveal insight into gene function and biochemical and genetic pathways. The sequences of genomes of some model organisms have been, or are about to be completely determined. Sequences homologous to the normal and 13-del mutant NC1 domain of collagen X will be screened for using bioinformatics tools in model organisms such as yeast, *C. elegans, Drosophila, zebrafish* and fugu. Molecular modelling of the normal and mutant NC1 domain may also yield insight into the possible interactions with other molecules.

B. Applied Studies for Clinical Applications

There are many different causes of dwarfism. Some are genetic, others environmental or endocrine. Some causes are known, others are as yet undetermined. A number of human conditions can result in a similar phenotype. However, work will need to be undertaken to determine whether they result from the same gene defect.

a. The mouse will serve as a useful model for testing the effect of drugs on growth, and the effect of surgical procedures on mice with collagen defects.

Drugs like growth hormone has been used to treat achondroplasia (Am J Med Genet Oct. 3, 1997;72(1):71–76) with limited effect. The effect of growth hormone in treating other bone dysplasia is not known. A mouse model is an ideal method whereby the effect of growth hormone on skeletal growth can be tested. Additionally, by understanding the basic mechanism by which short stature is produced, new drugs may be devised to stimulate bone growth in these conditions.

b. Surgical lengthening of bones can increase the height and limb lengths in dwarfs. This has been used to improve on their cosmetic appearance. However, while such bones can lengthen and heal in the lengthened position, what the optimal conditions are to perform the lengthening process is not known. The availability of a mouse model would allow experimentation using an external fixation device to perform lengthening at various rates and frequency. Additionally, by varying the mechanical characteristic of the external fixator the optimal mechanical environment for bone formation can be ascertained.

c. Of particular interest is that the additional bone formation is manifested by a thickening in the endosteal and cortical bone. If this process can be made use of in clinical practice, then it is of advantage over the currently available bone Induction agents (e.g. BMP2 and BMP7), as these agents result in bone formation in an uncontrolled manner, resulting in undesirable soft tissue and even muscle calcification.

There is the potential to enhance bone formation in conditions of low bone mass (osteoporosis), and to improve the quality and speed of bone union after fracture. This statement is made on the assumption that the endosteal bone formed is of normal mechanical characteristic and that the fracture healing occur uneventfully in these mice. Thus, experiments will be carried out to determine the mechanical properties of these bones under bending, tension, torsion and compression. Fracture healing will be assessed in these mice using an external fixation model, with the resultant fracture callus assessed mechanically and histologically. Molecular markers will be used to compare the healing process in Col10a1-13del mutant and wild-type mice.

Some possible ways of using this finding to increase bone mass may be:

i. Transfect the Col10a1-13del transgene into proliferating, hypertrophic chondrocytes and osteoblasts and assess the effect on in vitro mineralization using approaches reviewed by Bianco et al (35).

ii. To generate the mutant collagen X protein by recombinant DNA methodology and bacterial/eucaryotic cell/baculovirus protein expression systems. The recombinant protein can be implanted in the growth plate or bone and the effect on bone growth and fracture repair assessed. The protein may also be implanted at fracture sites. This may be tested out on normal and osteoporotic bone.

iii. Gene therapy, to deliver the Col10-13del construct Into cells at fracture sites or into osteoblasts in osteoporotic bone.

iv. to complement i)-iii) above, devise and generate vectors for inducible expression of the Col10-13del gene or the mutant peptide in the NCI domain. These vectors would be derived by modifications of the original Col10-13del construct by the addition of sequences which may activate expression on addition of an inducer and/or removal of a repressor. Further modifications can also be made to enable switching off of expression of this inducible gene. Such switching off of expression can be achieved by the addition of sequences which can bind repressors of transcription. These vectors may be used to generate transgenic mice in which the timing, site and level of expression of the transgene may be manipulated by induction. Suitable transgenic mice carrying the "inducer" will be generated and crossed to the Inducible Col10-13del mice.

This invention provides different use of the Col10-13del mice, the Col10a1 regulatory elements within the vector Col10-13del, and the novel peptide sequence created by the Col10a1-13del mutation for basic research into the regulation of bone growth and clinical applications for bone disorders. Specifically, this invention provides the use of the mouse as listed below and the use of the genes which have been affected by expression of the mutant type X collagen. Such genes can be used to develop tools to alter bone formation and growth.

The transgene or key molecules in the pathway revealed as a result of determining the underlying cause of the bone overgrowth can be modified for use in developing a gene or protein based therapy to treat bone and cartilage tumors by reversing or inhibiting chondrocytes proliferation.

The Col10-13del mouse may be used to:

1. identify key molecules and pathways important for the regulation of bone growth and treatment of dwarfism 1.1. To test the effect of drugs or other agents on stimulating bone growth.

Potential drugs for stimulating bone growth in dwarfism can be administered to transgenic and non-transgenic mice which are age and sex matched. The effect of the drug will be assessed by monitoring the animals weight, overall length, and also by measuring the length of the long bones and spine on radiographs taken at regular intervals. In addition, at set time intervals mice will be sacrificed and biochemical and immunohistochemical analyses will be carried out to test for the synthesis of bone-characteristic markers such as type I collagen, osteocalcin, alkaline phosphatase, matrix gla protein, osteonectin, etc.

Groups of control and test animals of different ages and sex will be used to assess the effect of the drug on different age and sex.

Potential drugs (including the use of recombinant human hormones) for increasing bone growth include but is not limited to the natriuretic peptide family of hormones (Yasoda, et al. Natriuretic peptide regulation of endochondral ossification. Evidence for possible roles of C-type natriuretic peptide/guanylyl cyclase-B pathway. J. Biol. Chem. 1998 273:11695–700), growth hormone (Kidder et al. Effects of growth hormone and low dose estrogen on bone growth and turnover in long bones of hypophysectomized rats. Calcif Tissue Int 1997 61:327–35; Rosen et al., Treatment with growth hormone and IGF-I in growing rats increases bone mineral content but not bone mineral density [published erratum appears in J Bone Miner Res Nov. 10, 1995; (11):1836] J Bone Miner Res 1995 10:1352–8.), estrogen (Kidder et al. Calcif Tissue Int 1997 61:327–35), insulin-like growth factor (Kidder et al. Calcif Tissue Int 1997 61:327–35), and parathyroid hormone (Coxam et al. Insulin-like growth factor 1 and parathyroid hormone effects on the growth of fetal rat metatarsal bones cultured in serum-free medium. Biol Neonate 1995 68:368–76) or any combination of the above. Other agents include but are not limited to the expression of a transgene which results in a local delivery of the hormones mentioned above in bone and growth plate (Yasoda, et al. J Biol Chem 1998 273:11695700), ultrasound, electromagnetic radiation, infrared and laser therapy and acupuncture.

1.2. To test the effect of surgery on increasing bone length.

A limb lengthening device (a modified external fixator that allows for a progressive change in the length of its connecting rods) will be attached to the mouse femur. The femur will then be osteotomised. When early callus formation is observed on radiographs, lengthening of femur will begin (callotaxis). Distraction will be performed under regular radiological monitoring. The frequency and the amount of distraction will be varied to assess the optimal conditions for callotaxis to occur. The animals will be sacrificed at various time points during distraction and at completion of the experiment. The femora will be harvested, and samples sent for mechanical testing and for histological analysis of the quality of the new bone formed.

A limb lengthening device is a modified external fixator that allows for a progressive change in the length of its connecting rods. A number of different systems are in common use today for increasing bone length in human subject (Dahl, M. T. and Fischer, D. A. Lower extremity lengthening by Wagner's method and by callus distraction. Orthop Clin Norh Am 1991 22:643–9; Hardy et al. The Sequoia circular fixator for limb lengthening. Orthop Clin North Am 1991 22:663–75; Price, C. T. and Mann, J. W. Experience with the Orthofix device for limb lengthening. Orthop Clin North Am 1991 22:651–61; Saleh, M. and Burton, M. Leg lengthening: patient selection and management in achondroplasia. Orthop Clin North Am 1991 22:589–99.

2. To test the effect of bone growth stimulating agents on fracture repair.

A fracture repair model in the mouse femur is set up using an externally fixed method (Andrew, J. G. and Gregory, J. An externally fixed murine fracture model. The 25th European symposium on calcified tissues. Bone vol.20, April 1997 p104S; Cheung et al. External fixation fracture model of the mouse femur. The HKOA annual congress, Nov. 15–16, 1997).

Procedure:

The femur will be exposed by an incision on the lateral aspect of the thigh. The vastus lateralis muscle is then split to directly expose the mid-shaft of the femur. The periosteum is not stripped to preserve the blood supply. The external fxator is applied using a drill guide to place the four pins. The femur is fractured after drilling holes midway between the pairs of pins; these holes act as a stress raiser to facilitate fracture. Skin is closed with an absorbable suture.

The bone growth stimulating agent will be administered to the mice after fracture. A second group of age and sex matched mice will also have the external fixator applied and the bone fractured. No bone growth stimulating agent will be used. This group will act as control.

Outcome will be monitored by regular radiographs, histological and mechanical testing of the harvested one after sacrifice. In addition biochemical, immunohistochemical and gene expression studies will be carried out to assess at the molecular level, whether bone is forming normally.

3. Treatment of human conditions which result in bone over-growth (including osteopetrosis) or mineralization abnormalities by drugs.

Bone overgrowth can occur locally or regionally as a result of certain tumors or iii response to certain agents such as physical trauma, ionising radiation, etc. Generalised bone overgrowth can occur in conditions like flurosis (excessive flouride admininstration) and osteopetrosis (cause unknown). In osteopetrosis, it is characterised by a generalized increase in the amount of bone and mineral content of the bone. Both the cortical and trabecular bone are affected with a resultant reduction in the marrow spaces within the medullary cavity. The cause of the condition is not known. The mouse may be used to:

i. Identify key molecules or pathways important for the regulation of bone growth and bone overgrowth.
ii. To make drugs which can be used to reverse or inhibit this process of bone overgrowth.
iii. Act as a model to test the effect of other drugs on reversing or inhibiting bone overgrowth.

Use of the Model to Identify Drugs for Treatment of Bone Overgrowth

By understanding the mechanism by which the Col10-13del transgene can cause bone overgrowth, and the regulatory pathways involved, a drug may be devised which can act as an inhibitor of bone growth for example one which inhibits osteoblast proliferation and/or differentiation. The drug may also be an antagonist to some key step in the regulatory pathway.

Use of the Model to Test the Effect of Drugs on Bone Overgrowth

The method involves adminstration of the drug to a group of transgenic animals, while another group of age and sex matched transgenic will be given a placebo to act as control. The effect of the drug on bone density will be assessed by regular radiological monitoring. Additionally, bone densitometry, micro-CT analysis or other more sensitive methods may be used in future to assess the effect of the drug on bone density. At regular time intervals the mice will be sacrificed and the bones examined histologically. Bone density may also be estimated using electron back-scattering analyses combined with electron microscopy. Histomorphometric analysis will be carried out to quantify the effect on the bone content. Biochemical and immunohistochemical analyses will also be carried out to study the level of synthesis of bone-characteristic markers such as type I collagen, osteocalcin, alkaline phosphatase, matrix gla protein, ostenectin, etc.

4. The transgene can be used or modified to be used as a method of regulating bone growth and switched on in conditions where more bone is required. For example— improving the amount of bone in patients with osteoporosis and increasing the rate of fracture healing using a gene therapy approach which may include an inducible/switchable approach as described above.

5. The mouse can be used to find potentially new genes and pathways responsible for regulating bone growth with implications for human bone disorders
6. If a human inherited condition caused by a regulatory defect in COL10A1 is found, the use of the mutation for diagnosis.
7. The use of the regulatory sequences in the transgene Col10-13del to target expression of therapeutic compounds to the growth plate by transgenesis.
8. The use of the novel peptide sequence in the NC1 domain created by the 13 bp deletion and antibodies raised against this sequence, if it should turn out to play a role in causing the abnormal bone growth.

Identification of Genetic Modifiers of Bone Growth

Since the severity of phenotype in the Col10-13del mice varied within a line, and these mice are essentially a combination of 129 sv/J, CBA and C57BL6 backgrounds, these mice will also serve as models to study the influence of genetic background on bone growth. Mice expressing the mutation on different bred background may be generated by breeding these mice to generate congenic mutant mice with different inbred background. Comparison of the phenotypic severity and extent of cartilage and bone growth will shed insight into the degree to which the bone overgrowth is affected by genetic background. Should differences in the bone overgrowth found in different inbred backgrounds, the mice could be used to identify genetic loci which account for genetic variation in bone growth. These loci may be detected using genetics, linkage analyses and highly polymorphic markers such as single nucleotide polymorphism (SNPs).

Molecular Consequences of Expressing the Mutant (Col10-12del) Protein in Hypertrophic Chondrocytes As discussed in section number iv above, the expression of the cell cycle regulator p57kip2 in the growth plates of non-trangenic and Col10-12del mice has been analyzed using immunohistochemistry (antibodies, gift of Dr. Anne Fergueson-smith, Dept of Anatomy, Cambridge University, UK). In non-transgenic controls, strong staining for p57kip2 was seen in the hypertrophic chondrocytes throughout the hypertrophic zone. However, the immunostaining showed areas of reduced staining within the hypertriphic zone of Col10-13del mice. Using antibodies to POCNA (Boehringer Mannheim), strong immunostaining was seen in hypertrophic chondrocytes of the Col10-13del mice which was not seen in the nontransgenic controls. These data are consistent with abnormal proliferation of the hypertrophic chondrocytes in the Col10-13del mice which may in part account for the expansion of the hypertrophic zone in these mice.

It has been suggested, as discussed in section number iv above, that there may be a problem with secreting the mutant collagent X protein in the transgenic mice (see experimental details above). Antibodies to the altered peptide sequence arising from the 13 del mutations have been generated (see experimental details in section number i above). Thi santibody has been used to stain growht plates sections from the Col10-13del and control mice. Immunostaining using antibodies specific to the mutant sequence in the Col10-13del protein shows strong intracellularly and almost undectable signal extracellularly. No staining was seen in non-transgenic samples. Comfirming the transgene specificity of the antibody. This data is consistent with an impaired ability to secrete the mutant protein. By contrast, immunostaining with antibodies to collagen X (gift of Bjorn Olsen, Harvard University) which would stain both the endogenous normal and mutant protein, showed an extracellular pattern of expression. The cells in the trabeculae may be hypertrophic chondrocytes in the cartilaginous remnants within trabeculae, or osteoblasts.

There was also increased staining of hypertrophic chondrocytes in the growth plate and cells in the trabeculae of Col10-13del mice using antibodies to heat shock protein 47 (hsp47), a chaperone of collagens (Ref: Expression K Matrix Biol 1998: 7 379–386). There was little staining with hsp47 in the hypertrophic chondrocytes of nontransgenic mice. Taken with the electron microscopy data showing the presence of engorged endoplasmic reticulum, this observation would be consistent with intracellular accumulation of protein due to difficulty with secretion and support hypothesis (see section f above).

Active degradation of intraceullular proteins can have significant implication on cellular behavior. Interaction of unfolded X chains with chaperones such as protein disulfide isomerase and Hsp47, glcoprotein-specific chaperones such as calnexin and calreticulin, BiP and Ubiquitin (see Ellis R J Molecular chaperones: pathways and netwotks, Curr Biol 1999 9:4 R137–139) will also be assessed in further studies by immuno-coprecipitation methods. This will give insights into the intracellular handling of unassembled collagen X chains and preferred pathway of clearance.

Expression has been seen (by in situ hybridization and by immunostaining) of the Col10-13del transgene in cells which are likely to be osteoblasts in the cortical bone. This finding indicates that expression of the mutant protein in both bone and hypertrophic cartilage may be the cause of the altered phenotype in Col10-13del mice.

In collaboration with Dr. Davine Opelstein (Biochemistry Dept, University of Hong Kong) the composition of the marrow cells in wild-type and Col10-13del transgenic mice has been analyzed. It was found that at 26 weeks of a age, a marked increase in the numbers of adipocytes. There alsoappeared to be an increased number of blood vessels in the bone. There appeared to be an inrease in the volume of the marrow cavity, and an abundance of total haematopoietic cells in wildtype compared to transgenic mice.

Consistent with an effect on haemetopoiesis was observation of abnormal morphology of the thymus in one of the transgenic mice. Further mice will need to be analyzed to determine if this is a consistent finding. These changes indicate an effect of the altered microenvironment of the transgenic bone on the development of cells within the marrow cavity. It is unknown if this is a direct effect or an indirect consequence whereby haematopoeitic cells remain constant by adipocytes are increased to compensate for the increased size of the marrow cavity in the transgenic mice. The mice are also closely monitored for signs of srthritis, such as rheumatoid arthritis or osteoarthritis).

REFERENCES

1. Mayne, R., and Irwin., M. H. (1986) in Articular cartilage biochemistry (Kuettner, K. E., Schleyerbach, R., and Hascall, V. C., eds) pp. 23–35, Raven Press, New York.
2. Schmid, T. M., and Linsenmayer, T. F. (1987) in Structure and Function of Collagen Types (Mayne, R., and Burgeson, R. E., eds) pp. 223–259, Academic Press, Orlando, Fla. 20.
3. Kong, R. Y. C., Kwan, K. M., Lau, E. T., Thomas, J. T., Boot-Handford, R. P., Grant, M. E., and Cheah, K. S. E. (1993) Eur. J. Biochem. 213, 99–111.
4. Schmid, T. M., and Linsenmayer, T. F. (1990) Dev. Biol. 138, 53–62.
5. Kwan, A. P. L., Cummings, C. E., Chapman, J. A., and Grant, M. E. (1991) J. Cell Biol. 14, 597–604.
6. Kirsch, T., and Pfaffle, M. (1992) FEBS Lett. 310, 143–147.

7. Anderson, H. C. (1989) Lab. Invest. 60, 320–330.
8. Kirsch, T., Swoboda, B., and Von der Mark, K. (1992) Differentiation 52, 89–100.
9. Gibson, G. J., Bearman, C. H., and Flint, M. H. (1986) Coll. Rel. Res. 6, 163–184.
10. Schmid, T. M., and Linsenmayer, T. F. (1985) J. Cell Biol. 100, 598–605.
11. Bonen, D. K., and Schmid, T. M. (1991) J. Cell Biol. 115, 1171–1178.
12. Schmid, T. M., Bonen, D. K., Luchene, L., and Linsenmayer, T. F. (1991) In Vivo 5, 533–540.
13. Poole, A. R., and Pidoux, I. (1989) J. Cell Biol. 109, 2547–2554.
14. Schmid, T. M., Popp, R. G., and Linsenmayer, T. F. (1990) Ann. NY Acad. Sci. 580, 64–73.
15. Warman, M. L., Abbott, M., Apte, S. S., Hefferon, T., McIntosh, I., Cohn, D. H., Hecht, J. T., Olsen, B. R., and Francomano, C. A. (1993) Nature Genet. 5, 79–82.
16. Wallis, G. A., Rash, B., Sweetman, W. A., Thomas, J. T., Super, M., Evans, G., Grant, M. E., and Boot-Handford, R. P. (1994) Am. J. Hum. Genet. 54,169–178.
17. Wallis, G. A. (1993) Curr. Biol. 3, 687–689.
18. McIntosh, I., Abbott, M. H., and Francomano, C. A. (1995) Hum. Mutat. 5, 121–125.
19. Lachman, R. S., Rimoin, D. L., and Spranger, J. (1988) Pediatr. Radiol. 18, 93–102.
20. Horton, W. A., and Hecht, J. T. (1993) in Connective tissue and its heritable disorders, molecular genetic and medical aspects (Royce, P. M., and Steinmann, B., eds) pp. 641–675, Wiley-Liss, New York.
21. Jacenko, O., LuValle, P. A., and Olsen, B. R. (1993) Nature 365, 56–61.
22. Jacenko, O., LuValle, P., Solum, K., and Olsen, B. R. (1993) Prog. Clin. Biol. Res. 383B, 427–436.
23. Rosati, R., Horan, G. S. B., Pinero, G. J., Garofalo, S., Keene, D. R., Horton, W. A., De Crombrugghe, B., and Behringer, R. R. (1994) Nature Genet. 8, 129–135.
24. K. M. Kwan, M. K. M. Pang, S. Zhou, S. K. Cowan, R. Y. C. Kong, T. Pfordte, B. R. Olsen, D. Sillence, P. P. L. Tam, & K. S. E. Cheah (1997) J. Cell Biol. 136 459–471.
25. Chan, D., Jacenko, O. (1998) Matrix Biol. 17:169–184.
26. Chan, D., Cole, W. G., Rogers, J. G., and Bateman, J. F. (1995) J. Biol. Chem. 270, 4558–4562.
27. Chan, D., Weng, Y. M., Hocking, A. M., Golub, S., McQuillan, D. J., and Bateman, J. F. (1996) J. Biol. Chem. 271, 13566–13572.
28. Horton, R. M., Hunt, H. D., Ho, S. N., Pullen, J. K., and Pease, L. R. (1989). Gene, 77:61–68.
29. Elima, K., Eerola, I., Rosati, R., Mets=E4ranta, M., Garofalo, S., Perala, M., de Crombrugghe, B., and Vuorio, E. (1993) Biochem. J. 289:247–253.
30. Cheah, K. S. E., Levy, A., Trainor, P. A., Wai, A. W. K., Kuffner, T., So, C. L., Leung, K. K. H., Lovell-Badge, R. H., and Tam, P. P. L. (1995) J. Cell Biol. 128, 223–237.
31. Vortkamp, A., Lee, K., Lanske, B., Segre, G. V., Kronenberg, H. M., and Tabin, C. J. (1996) Science 273, 613–622.
32. McCormick, C., Leduc, Y., Martindale, D., Mattison, K., esford, L. E., Dyer, A. P., and Tufaro, F. (1998) Nature Genetics 19:158–161.
33. Zhang, P., Liegeois, N. J., Wong, C., Finegold, M., Hou, H., Thompson, J. C., Silverman, A., Harper, J. W., DePinho, R. A., Elledge, S. J. (1997) Nature 387:151–158.
34. Yan, Y. Frisen, J., Lee, M-H., Massague, J., Barbacid, M. (1997) Genes & Dev. 11: 973–983.
35. Bianco, P., Cancedda, F. D., Riminucci, M., Cancedda, R. (1998) Matrix Biol. 17:185–192.
36. Nagata, K., (1998) Matrix Biol. 7:379–386.
37. Ellis, R. J., (1999) Curr. Biol. 9:4 R137–139.

What is claimed is:

1. An isolated DNA comprising the sequence as set forth in SEQ ID NO:2 which codes for a mutated collagen X or a portion thereof wherein the expression of the DNA regulates bone growth.

2. A vector which comprises the DNA of claim 1.

3. A method of production of a mutated collagen X polypeptide which regulates bone growth comprising (a) introducing the vector of claim 2 into a host cell, (b) culturing the host cell whereby the mutated collagen X golypeotide is expressed, and (c) isolating the mutated collagen X polypeptide.

4. The method of claim 3, wherein the host is either a prokaryotic or eukaryotic.

* * * * *